US006433783B2

(12) United States Patent
Murata

(10) Patent No.: US 6,433,783 B2
(45) Date of Patent: *Aug. 13, 2002

(54) OBJECT-IMAGE DISPLAYING APPARATUS

(75) Inventor: Yoshiyuki Murata, Ome (JP)

(73) Assignee: Casio Computer Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/767,121

(22) Filed: Jan. 22, 2001

Related U.S. Application Data

(63) Continuation of application No. 08/430,153, filed on Apr. 26, 1995, now Pat. No. 6,219,024, which is a continuation of application No. 08/170,504, filed on Dec. 20, 1993, now abandoned.

(30) Foreign Application Priority Data

Dec. 25, 1992 (JP) .............................................. 4-358313

(51) Int. Cl.⁷ ................................................ G09G 5/36
(52) U.S. Cl. ........................ 345/440; 345/630; 345/635
(58) Field of Search ................................ 345/156, 168, 345/169, 173, 440, 441, 203, 515, 629, 630, 635; 463/37; 434/307, 365, 169, 185

(56) References Cited

U.S. PATENT DOCUMENTS

| | | |
|---|---|---|
| 4,094,597 A | 6/1978 | Cloud |
| 4,695,976 A | 9/1987 | Nakanishi et al. |
| 4,813,013 A | 3/1989 | Dunn |
| 4,821,030 A | 4/1989 | Batson et al. |
| 5,029,312 A | 7/1991 | Goenner |
| 5,038,401 A | 8/1991 | Inotsume |
| 5,111,409 A | 5/1992 | Gasper et al. |
| 5,250,930 A | 10/1993 | Yoshida et al. |
| 5,289,568 A | 2/1994 | Hosoya et al. |
| 5,342,047 A | 8/1994 | Heidel et al. |
| 5,375,195 A | 12/1994 | Johnson |
| 5,383,027 A | 1/1995 | Harvey et al. |

FOREIGN PATENT DOCUMENTS

| | | |
|---|---|---|
| EP | 0275124 | 7/1988 |
| EP | 0379458 | 7/1990 |
| GB | 1605135 | 1/1982 |
| GB | 2275619 A | 9/1994 |
| JP | 03-129572 | 6/1991 |
| JP | 6-66775 | 9/1994 |
| WO | WO 91/04541 | 4/1991 |

OTHER PUBLICATIONS

Patent Abstracts of Japan, vol. 015, No. 344 (P–1245) and JP 03–129572 A (Hudson Soft Co. Ltd.), Jun. 3, 1991—English language Abstract only.

Patent Abstracts of Japan, vol. 16, No. 377 (P–1401) Aug. 12, 1992 & JP–A–04 118 781 (Sony Corp.) Apr. 20, 1992.

Primary Examiner—Kent Chang
(74) Attorney, Agent, or Firm—Frishauf, Holtz, Goodman & Chick, P.C.

(57) ABSTRACT

In an object-image displaying apparatus, a plurality of part designating switches disposed at positions corresponding respectively to locations of parts in an object image to be composed are operated to read out a part pattern of the relevant part from a part-pattern memory, which previously stores a plurality of part patterns of each of the parts. The read out part patterns are combined into an object image, and the combined object image is displayed on a display device and is printed by a printer. Further, a plurality of part designating switches provided respectively in correspondence to a plurality of part images displayed on the display device are operated to read out a part pattern of the relevant part from among plural sorts of part patterns stored in a memory. The read out part patterns are combined into an object image, and the object image is displayed on the display device and is printed by the printer.

6 Claims, 17 Drawing Sheets

FIG.5
HUMAN PART-PATTERN ROM
| PARTS \ NO. | 01 | 02 | | 50 |
|---|---|---|---|---|
| 1 OUTLINE | 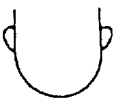 |  | |  |
| 2 HAIR STYLE |  |  | | 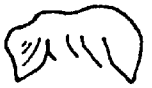 |
| 3 EYES |  |  | |  |
| ⋮ | | | | |
| 10 FEET |  |  | |  |
14B

FIG.6

PALM PART-PATTERN/ CONCLUSION-DATA ROM (A)

| PARTS \ NO. | | 01 | 02 | 50 |
|---|---|---|---|---|
| 1 | LIFE LINE |  |  |  |
| 2 | INTELLI-GENCE LINE | | | |
| 7 | FINGER PRINT |  |  |  |

14C (B)

| PARTS \ NO. | | 01 | 02 | 50 |
|---|---|---|---|---|
| 1 | LIFE LINE | A PERSON OF VITALITY, GIVING A VIVID IMPRESSION OTHERS. | A PERSON WHO IS GENTLE, KEEPS HIS OWN PACE. | A PERSON WHO IS UNDEMON-STRATIVE AND IS NOT TOUGH. |
| 2 | INTELLI-GENCE LINE | ROMANTICIST, CREATIVE PERSON. | A PERSON WHO USES PRUDENCE. | A PERSON WHO IS MORE INTUITIVE RICH IN INSPIRATION. |

FIG.7

DESPLAY REGISTER — 15

| DATA \ ITEMS | | NAME | ADDRESS/TEXT DATA AREA | | | | | MONTAGE-DATA AREA | | | | PALM-DATA AREA | | | |
|---|---|---|---|---|---|---|---|---|---|---|---|---|---|---|---|
| | | | AD-DRESS | PHONE NUMBER | AGE | HEIGHT | TEXT | OUT-LINE | HAIR STYLE | ... | FEET | LIFE LINE | INTELLI-GENCE LINE | ... | FINGER PRINT |
| 1 | A | OOO | OOO | 30 | 170 | OOO | 01 | 05 | ... | 06 | 05 | 04 | ... | 05 |
| | MEMBER 1 | — | — | 25 | 160 | OOO | 01 | 06 | ... | 06 | 05 | 03 | ... | 02 |
| | MEMBER 2 | — | — | 3 | 100 | OOO | 05 | 04 | ... | 05 | 04 | 03 | ... | 05 |
| | ... | ... | ... | ... | ... | ... | ... | ... | ... | ... | ... | ... | ... | ... |
| 2 | B | OOO | OOO | 80 | 160 | OOO | 05 | 04 | ... | 05 | 04 | 05 | ... | 06 |
| | MEMBER 1 | — | — | 90 | 158 | OOO | 04 | 07 | ... | 06 | 07 | 04 | ... | 07 |
| | MEMBER 2 | — | — | ... | 100 | OOO | 05 | 04 | ... | 07 | 06 | 05 | ... | 03 |
| | ... | ... | ... | ... | ... | ... | ... | ... | ... | ... | ... | ... | ... | ... |

155 — 152 — 153 — 154 — 156 — 157 — 150

MONTAGE-COMPOSING WORK AREA — 151

OBJECT-IMAGE DISPLAYING APPARATUS

This is a continuation of application Ser. No. 08/430,153 filed Apr. 26, 1995, now U.S. Pat. No. 6,219,024, which is a Continuation Application of Ser. No. 08/170,504, filed Dec. 20, 1993 (abandoned).

BACKGROUND OF THE INVENTION

1. Field of the Invention

The present invention relates to an object-image displaying apparatus which is capable of composing and displaying an image of a human being, an animal and a building.

2. Description of the Related Art

There has been known a so called montage composing apparatus, which is capable of composing an image of a human face in a similar manner in which a montage picture is produced. The montage composing apparatus is provided with a part-pattern memory which stores plural sorts of part patterns of each of face parts, the face parts composing an image of a human face, such as eyes, a nose, a mouth, eyebrows, an outline, a hair style and so on. Further, on the montage composing apparatus are installed a part-designating switch for designating a face part and a part-pattern selecting key for selecting one of a plurality of part patterns of the designated face part, which are operated during the process of composing a portrait or a face montage of a person.

With the above mentioned structure, a face part is selected at first by operation of the part-designating switch to compose a portrait of the person. For example, if an image of eyes in the portrait is composed, the face part "eyes" is designated first out of a plurality of face parts by operation of the part-designating switch. Then, one of the part pattern of the designated face part "eyes" is displayed on a display device. In place of the first displayed part patterns of the face part "eyes", other part patter of the "eyes" is selected and displayed from among the plurality of part-patterns of the "eyes" by operation of the part-pattern selecting switch. Further, another part pattern of the "eyes" is displayed instead of the last displayed part pattern by the following operation of the part-pattern selecting switch. In this way, a desired part pattern of the "eyes" can be selected and displayed on the display device by operation of the part-pattern selecting switch.

When the desired part pattern of the "eyes" is determined, other face parts, for example, a face part "nose" is selected by operation of the part-designating switch. Then, a part pattern of the face part "nose" is displayed on the display device. Another part pattern of the "nose" is displayed in place of the first displayed part pattern by operation of the part-pattern selecting switch. A different part pattern of the "nose" is successively displayed in place of the last displayed part pattern every operation of the part-pattern selecting switch.

When the desired part pattern of the "nose" is determined, another face part, for example, a face part "mouth" is selected by operation of the part-designating switch.

In this manner, with respect to other face parts: "eyebrows", "outline", "hair style" and so on, similar operations are performed to determine desired part patterns of the individual face parts. Finally, the selected part patterns of the respective face parts are combined to compose the portrait or the face montage of the person.

As described above, in the conventional montage composing apparatus, the part designating switch and the part-pattern selecting switch have to be alternatively operated each time a face part is designated and a relevant part pattern of the designated face part is selected. The conventional montage composing apparatus requires a user to do complex operations, and it will take a great deal of time to complete the portrait accordingly, whereby a desired portrait can not be made easily in a short time.

SUMMARY OF THE INVENTION

The present invention has been made to overcome the above mentioned inconvenience involved in the prior art, and has an object to provide an object-image composing apparatus which is capable of composing and displaying a desired image or a montage of an object with easy operation.

According to one aspect of the invention, there is provided an object-image displaying apparatus which comprises:

part-pattern memory means for storing plural sorts of part patterns, each sort of part patterns representing one of parts which compose an object;

display means for displaying an image of the object;

a plurality of operation switch means disposed at positions corresponding respectively to locations of the parts in an object image to be composed, each for reading out a part pattern of the relevant part from said part-pattern memory means; and display control means for controlling said display means to display an object image composed of a combination of part patterns read out by said plurality of operation switch means.

According to other aspect of the invention, there is provided an object-image displaying apparatus comprising:

first display means for displaying a plurality of part images composing an image of an object;

part-pattern memory means for storing plural sorts of part patterns, each sort of part patterns representing one of parts which compose an object;

a plurality of operation switch means provided, respectively, in correspondence to the plurality of part images displayed on said first display means, each for reading out a part pattern of the relevant part from said part-pattern memory means; and second display means to display an object image composed of a combination of part patterns read out by said plurality of operation switch means.

According to further aspect of the invention, there is provided an object-image displaying apparatus comprising:

part-pattern memory means for storing plural sorts of part patterns, each sort of part patterns representing one of parts which compose an object;

first display means for displaying a first object image which is composed of a combination of a plurality of part patterns, the part patterns representing parts composing the object respectively;

a plurality of operation switch means provided respectively in correspondence to the parts composing the object, each for reading out a part pattern of the relevant part from said part-pattern memory means;

part-pattern substituting means for substituting a part pattern read out by said plurality of operation switch means for the relevant part pattern originally included in the first object image displayed on said first display means; and second display means for displaying a second object image which is composed of a combination of both the part patterns originally included in the first object image and the part patterns substituted by said part-pattern substituting means.

According to yet another aspect of the invention, there is provided an object-image displaying apparatus comprising:

part-pattern memory means for storing plural sorts of part patterns, each sort of part patterns representing one of parts which compose an object;

display means for displaying an object image which is composed of a combination of a plurality of part patterns, the part patterns representing parts composing the object respectively;

a plurality of operation switch means provided on said display means respectively in correspondence to the parts included in the object image displayed on said display means, each for designating a part pattern among a sort of part patterns of the relevant part stored in said part-pattern memory means;

reading means for reading out a part pattern designated by said operation switch means; and display control means for controlling said display means to display an object image composed of a combination of the part patterns read out by said reading means.

It would be apparent to those skilled in the art from the following description of preferred embodiments that the present invention may be modified in various manner and may be applicable to other apparatus.

BRIEF DESCRIPTION OF THE DRAWINGS

Other objects and structures of the present invention will be more fully understood from the description, when taken in conjunction with the accompanying drawings, in which:

FIG. 5 is a schematic view illustrating states in which part patterns for a human are stored in a part-pattern ROM;

FIG. 6 is a schematic view illustrating states in which part patterns for a palm and conclusion data are stored in a palm/conclusion ROM;

FIG. 7 is a schematic view showing various data stored in a RAM;

DETAILED DESCRIPTION OF THE PREFERRED EMBODIMENTS

Now, preferred embodiments of the present invention will be described with reference to the accompanying drawings.

First Embodiment

Figure 1:
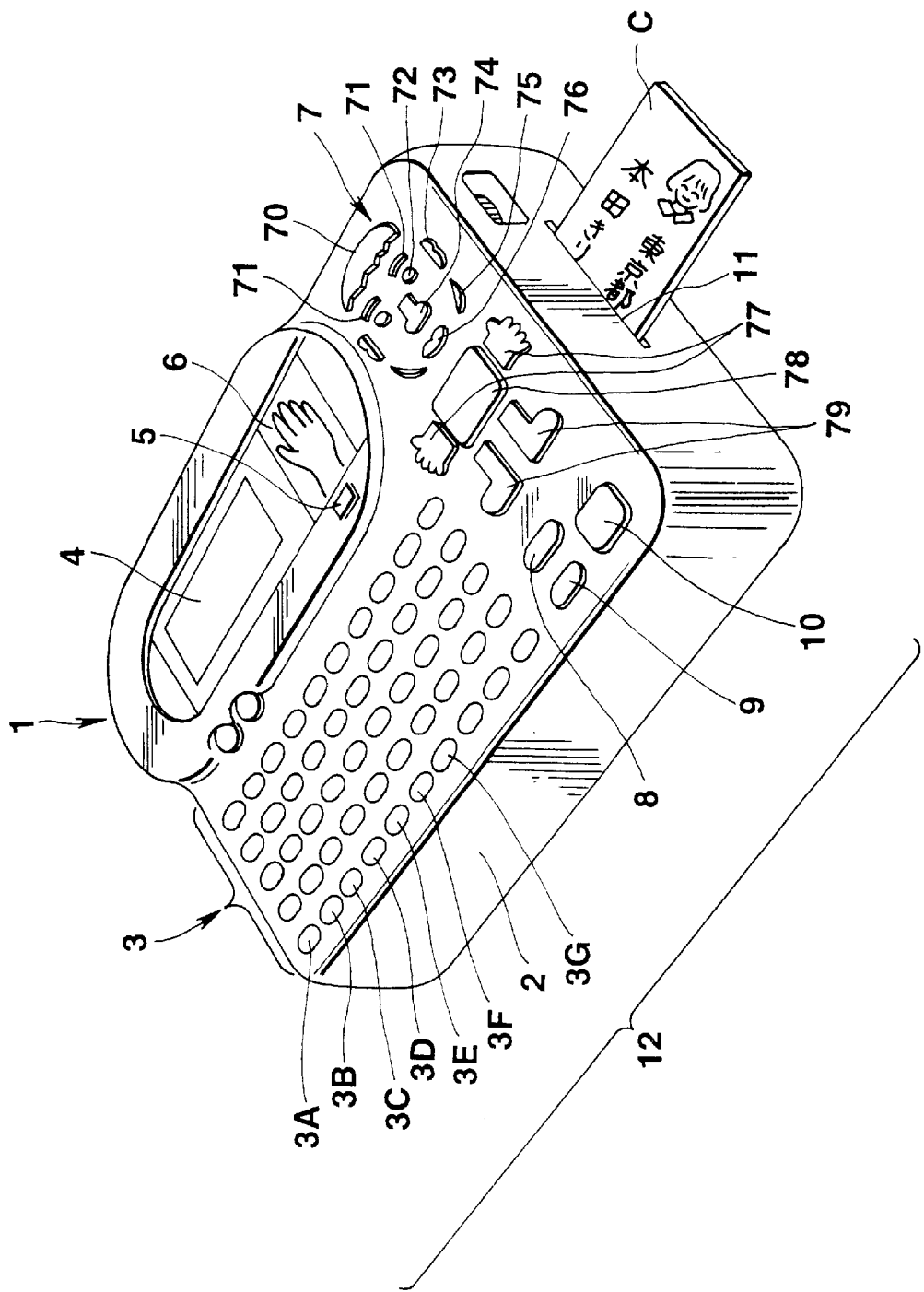
FIG. 1 is an external perspective view of a displaying/printing apparatus incorporating an embodiment of the present invention.
Figure 2:
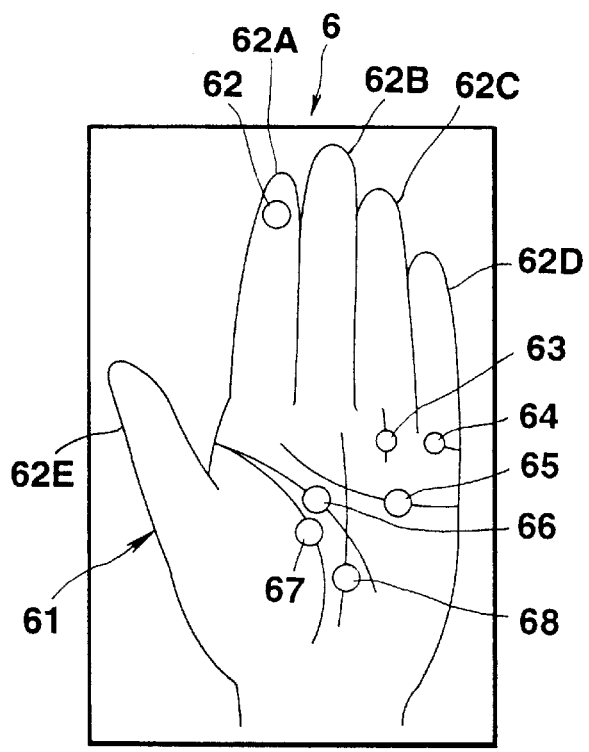
FIG. 2 is an enlarged view of a palm-data input unit.
Figure 3:
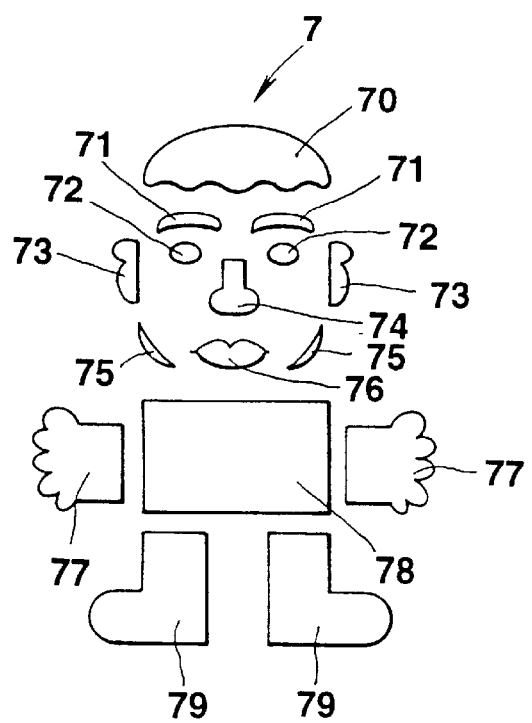
FIG. 3 is an enlarged detailed view of a montage-data input unit.
Figure 4:
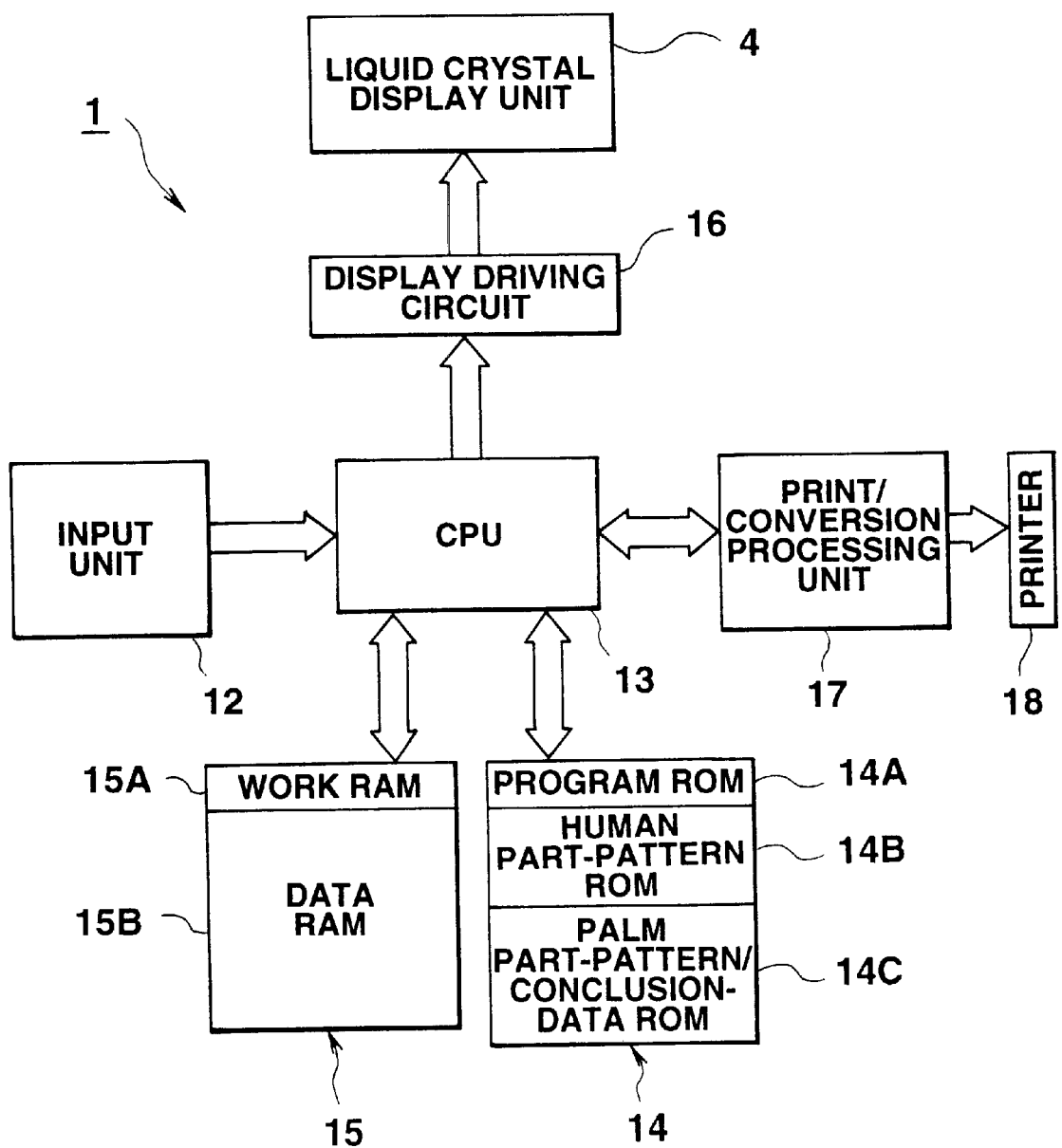
FIG. 4 is a circuit diagram of the embodiment of the present invention.

FIG. 1 is an external perspective view of a displaying/printing apparatus incorporating an embodiment of the present invention. FIG. 2 is an enlarged view illustrating a palm-data input unit in detail. FIG. 3 is an enlarged view illustrating a montage-data input unit in detail. FIG. 4 is a block diagram of the first embodiment of the invention.

In FIG. 1, the displaying/printing apparatus 1 has an external casing 2. On an upper surface of the casing 2, there are provided an input unit 3 including a plurality of switches and a liquid crystal display unit (hereafter, sometimes referred to as a display unit) 4. A palm-montage composing switch 5 and a palm-data input unit 6 are provided in vicinity to the liquid crystal display unit 4. On the palm-data input unit 6 is drawn a palm 61 of a left hand of a person as shown in FIG. 1. The enlarged left hand palm 61 is shown in FIG. 2. Further, there are drawn several lines such as a health line, a marriage line, a heart line, an intelligence line, a life line and a fortune line (a job line) in the drawn palm 61. As shown in FIG. 2, a fingerprint switch 62 is disposed at a finger tip 6A of the left hand palm 61 drawn on the palm-data input 6. Though the fingerprint switch 62 is provided only at the tip of the index finger 62A in the present embodiment, fingerprint switches may be provided at each of the tips of the fingers 62B–62E. In addition to the fingerprint switch 62, there are provided a health-line switch 63, a marriage-line switch 64, a heart-line switch 65, an intelligence-line switch 66, a life-line switch 67 and a job-line switch 68, respectively, on the health line, the marriage line, the heart line, the intelligence line, the life line and the job line on the drawn palm 61.

Further, there are provided on the upper surface of the external casing 2 a montage-data input unit 7, a human-montage composing switch 8, a data-input switch 9 and a register switch 10. An input unit 12 is composed of the montage-data input unit 7, the human-montage composing switch 8, the data-input switch 9 and the register switch 10. An outlet 11 for discharging a card C, which is printed by a printer 18 (see FIG. 4) mounted in the casing 2, is provided on a side wall of the external casing 2. As shown in an enlarged view of FIG. 3, the montage-data input unit 7 is composed of a plurality of part-designating switches 70–79, and these switches 70–79 are disposed at relevant locations on the surface of the external casing 2, which locations correspond respectively to positions of parts in a montage of a human body to be composed. More specifically, the montage-data input unit 7 includes a hair-style switch 70, eyebrow switches 71, eye switches 72, ear switches 73, a nose switch 74, outline switches 75, a mouth switch 76, hand switches 77, a dress switch 78 and feet switches 79. The hair-style switch 70, the eyebrow switches 71, and other switches have shapes which correspond respectively to parts of the montage to be composed, each of which parts is designated by the relevant switch. In other words, for example, the hair-style switch 70 is made in a shape similar to a hair style and the eyebrow switches are made in a shape similar to eyebrows.

FIG. 4 is a circuit diagram of the embodiment of the displaying/printing apparatus 1. In FIG. 4, operation data of the switches such as the hair-style switch 70 and the eyebrow switches 71 of the input unit 12 are entered to a central processing unit (CPU) 13. In accordance with a program stored in a program ROM 14A of a ROM 14, the CPU 13 performs a control operation of the displaying/printing apparatus 1 on the basis of data stored in a work RAM 15A of a data RAM 15. Further, the CPU 13 controls a display driving circuit 16 which drives the liquid crystal display unit 4. The CPU 13 controls a print/conversion processing unit 17 to convert montage data and character data entered from the input unit 12 into printing data. The printer 18 performs a printing operation in accordance with a signal output from the print/conversion processing unit 17.

The ROM 14 is composed of the program ROM 14A, a human part-pattern ROM 14B shown in FIG. 5 and a palm part-pattern/conclusion-data ROM 14C shown in FIG. 6. As shown in FIG. 5, the human part-pattern ROM 14B stores fifty (50) sorts of human part-patterns for each of 10 parts such as "outline", "hair style", "eyes", . . . , and "feet", which correspond respectively to the part-designating switches 70–79 of the montage-data input unit 7. The above 50 sorts of human part-patterns are different in shape, and are stored in relevant areas in the ROM 14B, to which areas numbers "01"–"50" are assigned, respectively. The palm part-pattern/conclusion-data ROM 14C includes a palm part-pattern area (A) and a conclusion-data area (B), as shown in FIG. 6. Fifty (50) sorts of palm part-patterns for each of 7 parts such as "life line", "intelligence line", . . . , and "fingerprint", which correspond respectively to part-designating switches 62–68 of the palm-data input unit 6, are stored in relevant areas corresponding respectively to numbers "01"–"50" in the palm part-pattern area (A) are stored. Fifty (50) sorts of conclusion data of palm reading or fortunetelling with respect to each of the 7 parts such as "life line", "intelligence line", . . . , and "fingerprint" are stored in relevant areas of the conclusion-data area (B), which areas correspond respectively to numbers "01"–"50". In short, 350 sorts (50 part patterns for each of 7 parts) of conclusion data in total are stored in the conclusion data area (B).

The data RAM 15 includes a display register 150, a work area 151 for composing a montage, and a data area 152 for storing data of a person and his (her) family for each of items 1, 2 and so on. As shown in FIG. 7, each of the items in the data area 152 consists of a personal data area 153 for storing personal data of the person: Mr. A or Mr. B, and family-data areas 154 for storing data of members of family of Mr. A or Mr. B.

The personal data area 153 and the family data areas 154 are divided into an address/text data area 155, a montage-data area 156 and a palm-data area 157. The address/text data area 155 stores address/text data such as names and addresses of the persons and members of his (her) family. As shown in FIG. 7, in relevant part areas of the montage-data area 156 are stored montage data or pattern numbers (shown in FIG. 5) corresponding part-patters of each of the parts such as "outline", "hair style", "eyes" and so on, which patterns are input by operations of the part-designating switches 70–79 of the montage-data input unit 7. Further, as shown in FIG. 7, in relevant part areas of the palm-data area 157 are stored palm data or pattern numbers (shown in FIG. 6) corresponding palm part-patters of each of the parts such as "life line", "intelligence line", "fingerprint" and so on, which part patterns are input by operations of the part-designating switches 62–68 of the palm-data input unit 6.

Operation of the First Embodiment

Now, operation of the first embodiment with the above mentioned structure will be described with reference to flow charts of FIGS. 8–14.

Figure 8:
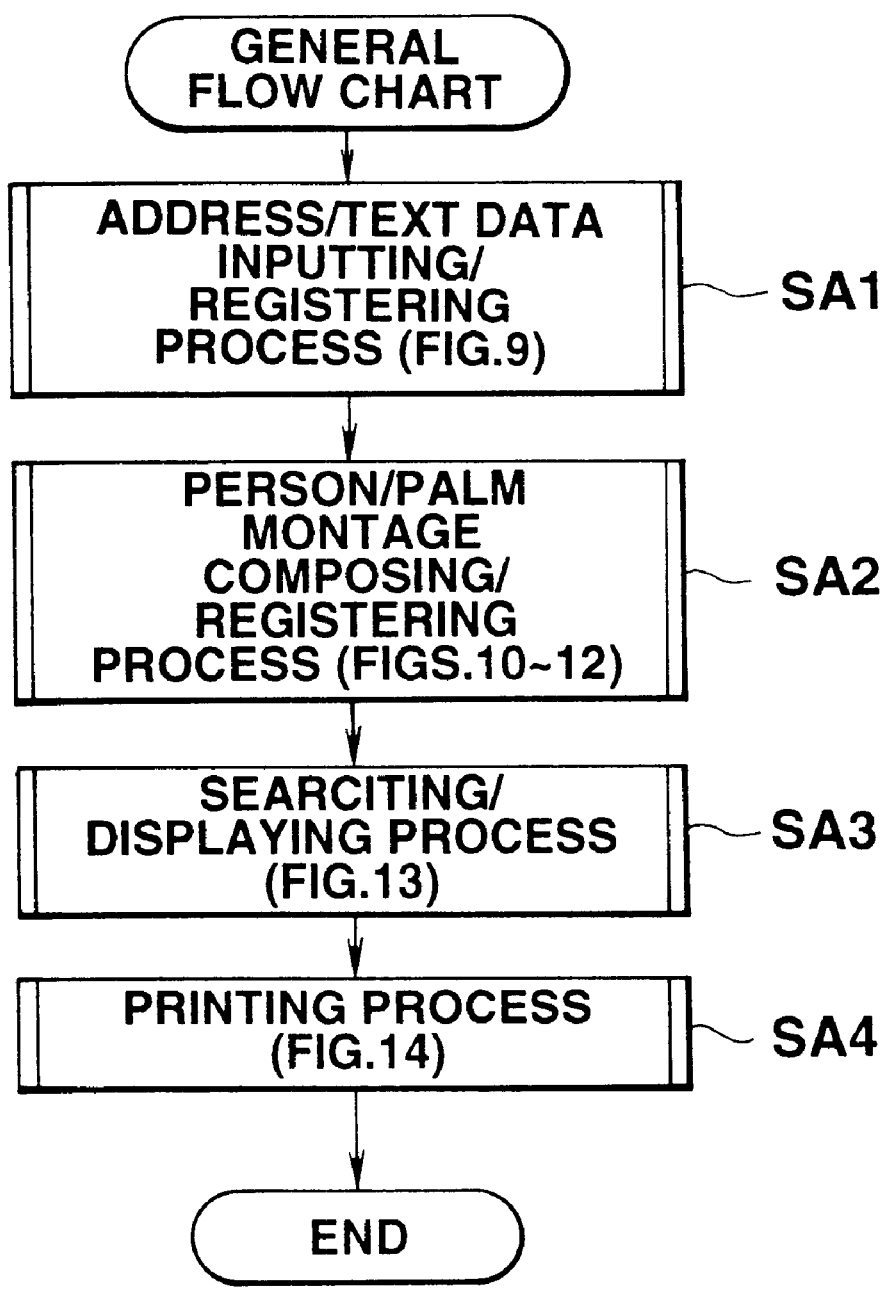
FIG. 8 is a general flow chart of operation of the embodiment of the displaying/printing apparatus.
Figure 9:
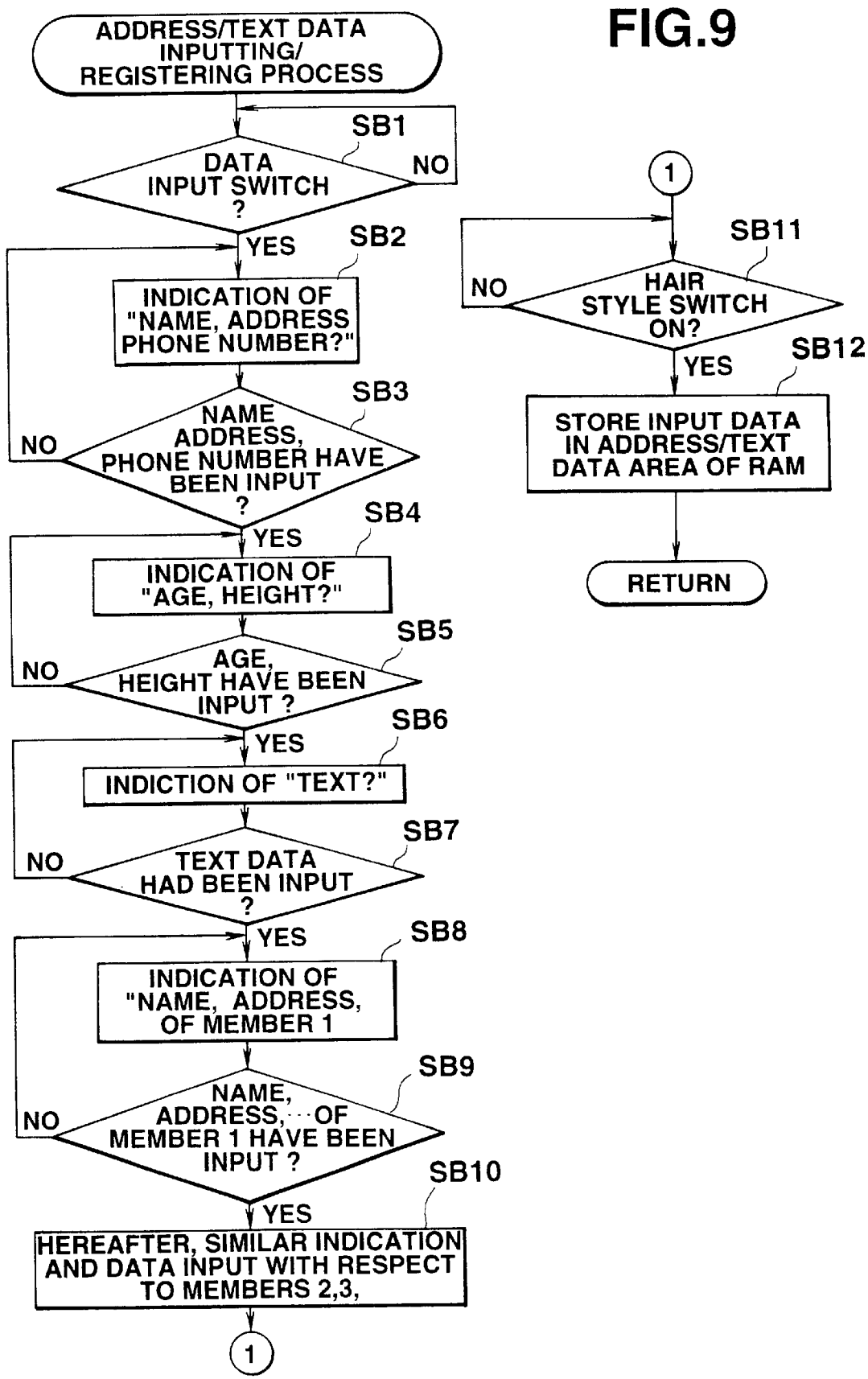
FIG. 9 is a flow chart of a process for inputting and registering address and text data.

FIG. 8 is a general flow chart of the operation of the first embodiment. FIGS. 9–14 are flow charts of processes executed at individual steps of the general flow chart of FIG. 8. At step SA1 of the general flow chart of FIG. 8, an inputting/registering process is performed, wherein address data and text data or text data are entered. The inputting/registering process is performed to input address data and text data in accordance with a flow chart of FIG. 9. In the inputting/registering process, it is judged at step SB1 of FIG. 9 whether the data-input switch 9 has been operated. When the data-input switch 9 has been operated, an indication of "name, address, phone number?" is displayed on the liquid crystal display unit 4 at step SB2, thereby requesting a user of the apparatus to input an address and text data. At the following step SB3, it is Judged whether a name, an address and a phone number have been input. Processes at steps SB2 and SB3 are repeatedly performed until these data: "name", "address" and "phone number" have been input. During the processes at steps SB2 and SB3, the user inputs these data: "name", "address" and "phone number" by operation of switches of the input unit 3.

When the data: "name", "address" and "phone number" have been input, a next indication of "age, height?" is displayed on the display unit 4 at step SB4. At step SB5, it is judged whether data: "age" and "height" have been input. Processes at steps SB4 and SB5 are repeatedly performed until these data: "age" and "height" have been input. During the processes at steps SB4 and SB5, the user inputs these data: "age" and "height" by operation of switched of the input unit 3. When the data: "age" and "height" have been input, an indication of "text?" is displayed at step SB6, thereby requesting the user to input text data. At step SB7, it is judged whether text data has been input.

When the text data has been input, an indication of "name, address, phone number, age and height of a member 1 of the family?" is displayed at step SB8, thereby requesting the user to input these data: "name" "address", "phone number", "age" and "height" of the member 1 of the family. It is judged at step SB 9 whether all the data of the member 1 have been input. When all the data of the member 1 have been input, data: "name, address, phone number, age and height of members 2, 3 and so on of the family are input in a similar manner described above.

When all the necessary data have been input, it is judged at step SB11 whether the register switch 10 is operated. When the register switch 10 has been operated, the data: "address" and "text data" that have been input are stored in the address/text data area 155 of the RAM 15 at step SB12, and operation returns to the general flow chart of FIG. 8.

Figure 10:
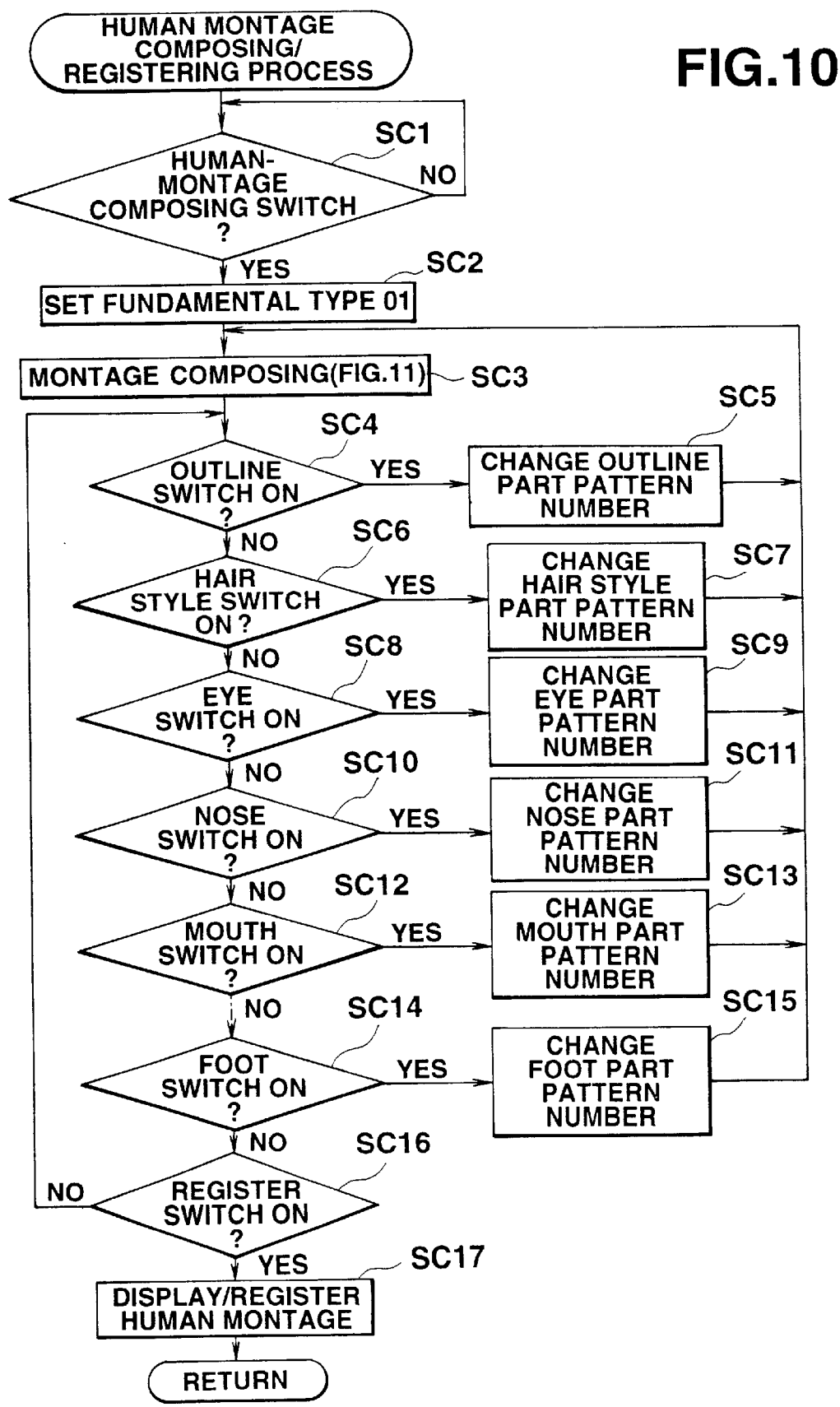
FIG. 10 is a flow chart of a montage composing/registering process for composing and registering a human montage.
Figure 11:
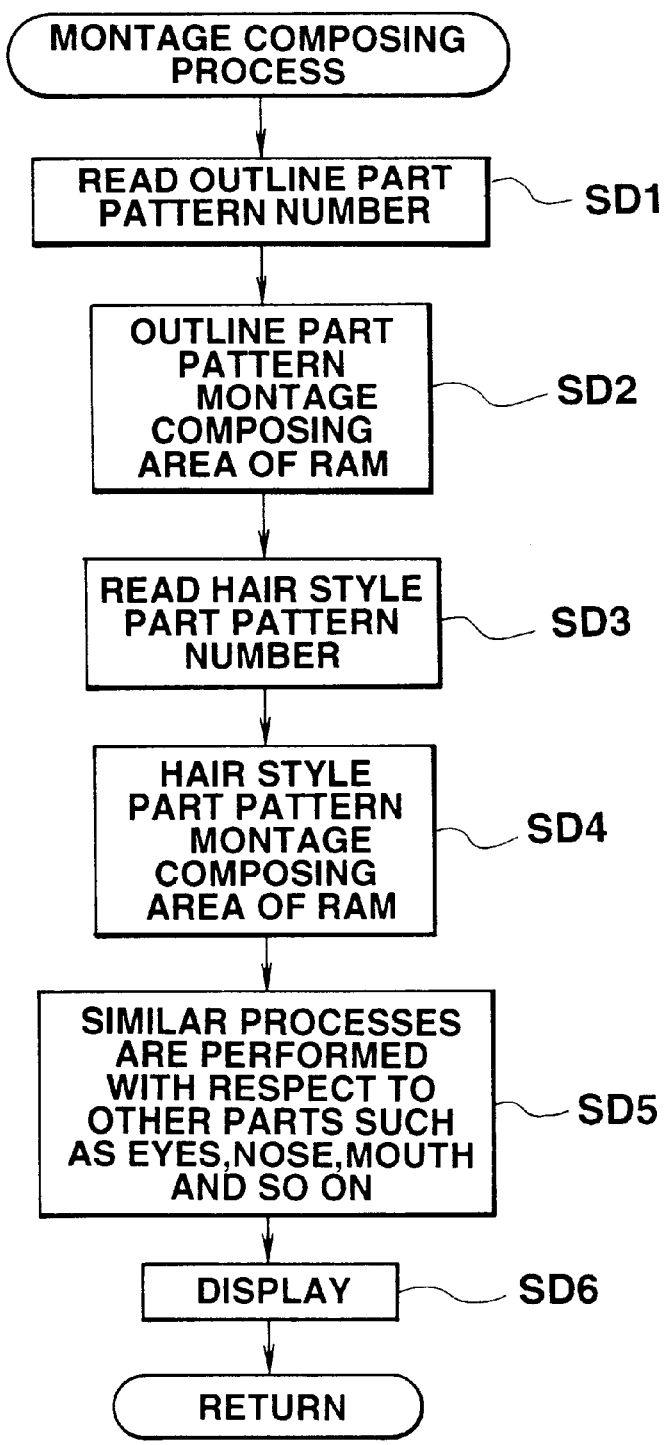
FIG. 11 is a flow chart of a montage-data combining process.
Figure 12:
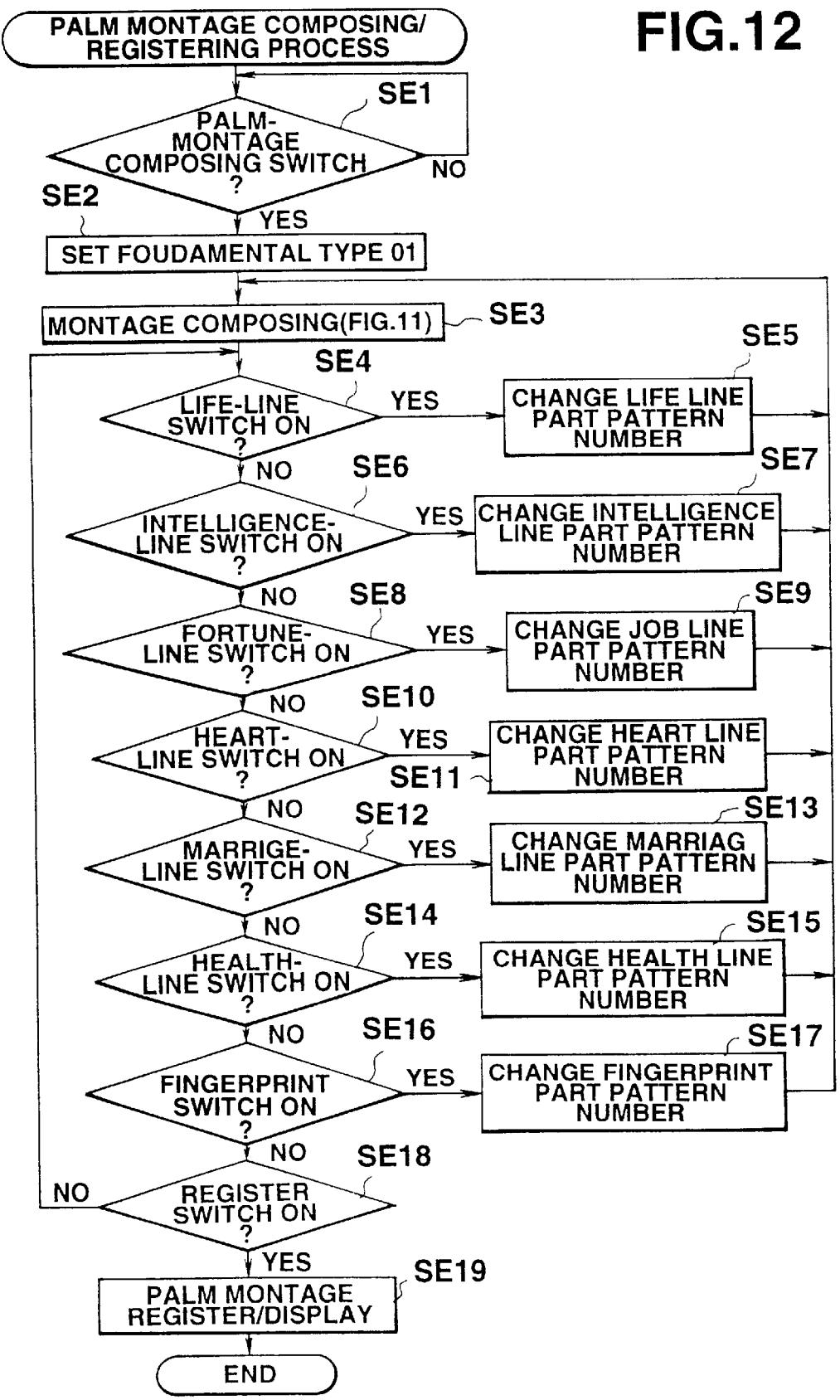
FIG. 12 is a flow chart of a montage composing/registering process for composing and registering a palm montage.

At step SA2 of the general flow chart of FIG. 8, a montage composing/registering process is performed, where montages of a person and a palm are composed and registered in accordance with flow charts of FIGS. 10–12. The montage composing/registering process that composes and registers the montage of a person is performed in accordance with the flow chart of FIG. 10.

More specifically, the montage composing/registering process of a person starts with operation of the human-montage composing switch 8 at step SC1. When it is determined at step SC1 that the human-montage composing switch 8 has been operated, a montage of a fundamental type "01" is initially set at step SC2 to display a fundamental montage of a person of an initial setting stage. The montage of a fundamental type "01" is a combination of part-pattern numbers "01" for ten parts: "outline" 1, "hair style" 2, "eyes" 3, . . . and "feet" 10, which are stored respectively in relevant areas in a column of "01" of the human part-pattern ROM 14B shown in FIG. 5. Therefore, ten part-pattern numbers "01" for all the parts (a part-pattern number "01" of the part of "outline" 1 to a part-pattern number "01" of the part of "feet" 10, all data for one person) are initially set respectively in part areas of the montage-data area 156 of the data RAM 15 at step SA2.

Then, a montage composing process is performed at step SC3. In accordance with a flow chart of FIG. 11, the montage composing process is performed based on the part-pattern numbers of the fundamental type "01" or based on the part-pattern numbers stored in the montage-data area 153.

More specifically, in the montage-composing process of FIG. 11, the part pattern number of the part "outline" 1 is read out from among the initially set part-pattern numbers, at step SD1, and an outline pattern corresponding to the read out part pattern number "01" of the part "outline" is read out from the relevant area in the column of "01" of the part-pattern ROM 14B, and is transferred to a montage-composing area 151 of the data RAM 15 at step SD2. Then, a part pattern number "01" of the part "hair style" is read out from among the initially set part-pattern numbers at step SD3, and a hair style pattern corresponding to the read out part pattern number "01" of the part "hair style" is read out from the relevant area in the column of "01" of the part-pattern ROM 14B, and is transferred to the montage-composing area 151 of the data RAM 15 at step SD4. Similarly, processes are performed with respect to other parts: "eyes", "nose", "mouth" and so on at step SD5, and part patterns for the parts are transferred to the montage-composing area 151 to be combined therein. The composed montage is displayed on the liquid crystal display unit 4 at step SD6. Therefore, at the initial setting time immediately after the montage-composing switch 8 has been operated, the montage of the fundamental type is displayed on the liquid crystal display unit 4 at step SD6. The fundamental type of montage of a full-length figure is composed of the part patterns which correspond respectively to the part-pattern numbers "01" of the respective parts: from "outline" to "feet" and are stored in corresponding areas in the column "01" in the part-pattern ROM 14B of FIG. 5.

Meanwhile, at step SC3 of FIG. 10 and the following steps, it is judged whether the part-designating switches 70–79 are operated and processes associated therewith are performed.

It is judged at step SC4 of FIG. 10, whether an outline switch 75 has been operated. When it is determined that the outline switch 75 has been operated, the part-pattern number "01" of the part "outline", which has been initially set at an outline area of the montage-data area 156, is renewed to "02" and transferred by operation of the outline switch 75 at step SC5, and then is subjected to the part-pattern combining process at step SC3. Therefore, only the part pattern "01" corresponding to the part "outline" is replaced with the part pattern which corresponds to the part-pattern number "02" of the part "outline" designated by operation of the outline switch 75. In this manner, the part pattern of the part "outline" included in the montage of the full-length figure displayed on the display unit 4 is sequentially renewed and displayed every operation of the outline switch 75. Since 50 sorts of part patterns of the part "outline" are stored, 50 part patterns of the part "outline" can be substituted for the corresponding part pattern included in the montage of the full-length figure displayed on the display unit 4 by operation of the outline switch 75. Therefore, a desired part pattern of the part "outline" or a part pattern most similar to the desired part pattern can be selected from among 50 sorts of part patterns, and can be displayed on the display unit 4.

When it is determined at step SC4 that the outline switch 75 has not been operated, it is judged at step SC6 whether a hair style switch 70 has been operated. When a hair-style switch 70 is operated, the part pattern number "01" of the part "hair style" which is registered in a hair-style area of the montage-data area 156 will be changed to the part-pattern number "02" of the part "hair style" designated by operation of the hair-style switch 70, and registered in the hair-style area of the montage-data area 156 at step SC7. Therefore, only the part pattern "01" of the part "hair style" is replaced with the part pattern corresponding to the part-pattern number "02" of the part "hair style" designated by operation of the hair-style switch 70. Since 50 sorts of part patterns of the part "hair style" are stored, 50 part patterns of the part "hair style" can be substituted for the corresponding part pattern included in the montage of the full-length figure displayed on the display unit 4 by operation of the hair-style switch 70.

Similarly, it is judged respectively at steps SC8, SC10, SC12, SC14 whether the switches 72–79 have been operated. When the switches 72–79 (from an eye switch 72 to a feet switch 79) are operated, corresponding part-pattern numbers are changed to desired part-pattern numbers, respectively. In this manner, every part-pattern number can be changed to a part-pattern number corresponding to the desired part pattern or corresponding to a part pattern most similar to the desired part pattern. As a result, a montage of the full-length figure or a portrait can be displayed on the display unit 4, which has been modified by the user based on the initially displayed fundamental style of montage of the full-length figure.

When a desired montage is displayed on the display unit 4, a register switch 10 is operated, or characters "O" and "K" are entered by operation of the alphabet switches. Then, the operation goes from step SC16 to step SC17, where the part-pattern numbers of the parts designated by the part-designating switches 70–79 are stored, as montage data, respectively in relevant part areas of the montage data area 156, which part areas correspond to areas of the address/text data area 155 where the name of the relevant person, and his (or her) personal data have been stored in accordance with the flow chart of FIG. 9. When the process of registering and displaying the composed montage has been finished, the operation returns to a process at step SA3 of the general flow chart of FIG. 8.

In the meantime, a montage composing/registering process of composing and displaying a palm montage will be performed in accordance with the flow chart of FIG. 12. The process starts with operation of the palm-montage composing switch 5 at step SE1. When it is determined that the palm-montage composing switch 5 has been operated, the palm montage of a fundamental type "01" is initially set at step SE2 to display the palm montage at an initial setting stage. The palm montage of the fundamental type "01" is a combination of all part-pattern numbers stored in areas in the column of "01", which areas correspond respectively to seven parts (from "life line" to "fingerprint") stored in areas in the column of "01" of a palm-data area (A) shown in FIG. 6. All part-pattern numbers of a palm which correspond respectively to seven part patterns ("life line" to "fingerprint") composing a palm montage are initially set respectively in the part areas of the palm-data area 157 of the RAM 15.

Then, the montage-composing process is performed at step SE3. In a similar manner described with respect to the composing/registering process of a person, the montage-composing process is performed based on the part-pattern numbers of the fundamental type "01" in accordance with a flow chart of FIG. 11. Therefore, at the initial setting stage, the palm montage of the fundamental type is displayed on the liquid crystal display unit 4, which palm montage is composed at step SE3 by combining the part patterns of the "heart line", "intelligence line", "fingerprint", "health line", "marriage line" and "fortune line", which are stored in the areas in the column of "01" of FIG. 6.

Meanwhile, during processes at steps SE4–SE17 of FIG. 12, it is judged whether the switches 62–68 (from a fingerprint switch 62 to a life-line switch 68) have been operated and associated part-pattern number changing processes are executed. More specifically, it is judged at step SE4 whether the life-line switch 68 has been operated. When it is determined that the life-line switch 68 has been operated, a life-line part number, which has been initially set to "01", is renewed to "02" and registered at step SE5, and then is subjected to the above montage-composing process at step SE3. Therefore, only the part pattern of the part "life line" corresponding to the initially set part-pattern number "01" is replaced with the part pattern corresponding to the part-pattern number "02" designated by the life-line switch 68. Every operation of the life-line switch 68 successively changes only the part pattern of the "life line" combined in the palm montage displayed on the liquid crystal display unit 4. Since 50 sorts of part patterns of the part "life line" are stored, 50 part patterns of the part "life line" can be successively changed by successive operations of the life-line switch 68. Therefore, a part pattern of the life-line which has the best resemblance to that of the person can be selected out of 50 sorts of part patterns and displayed on the display unit 4.

When it is determined that the life-line switch 68 has been operated, it is judged at step SE6 whether an intelligence-line switch 66 has been operated. When a result of judgment at step SE6 is "YES", the part-pattern number of the part "intelligence line" will be changed from "01" to "02" at step SE7. Then, the part pattern corresponding to the part-pattern number "01" of the part "intelligence line" is changed to a part pattern corresponding to part-pattern number "02". Similarly, since 50 sorts of part patterns of the part "intelligence line" are stored, the part pattern of the part "intelligence line" can be selected out of 50 sorts of part patterns by operation of the intelligence-line switch 66.

Figure 15:
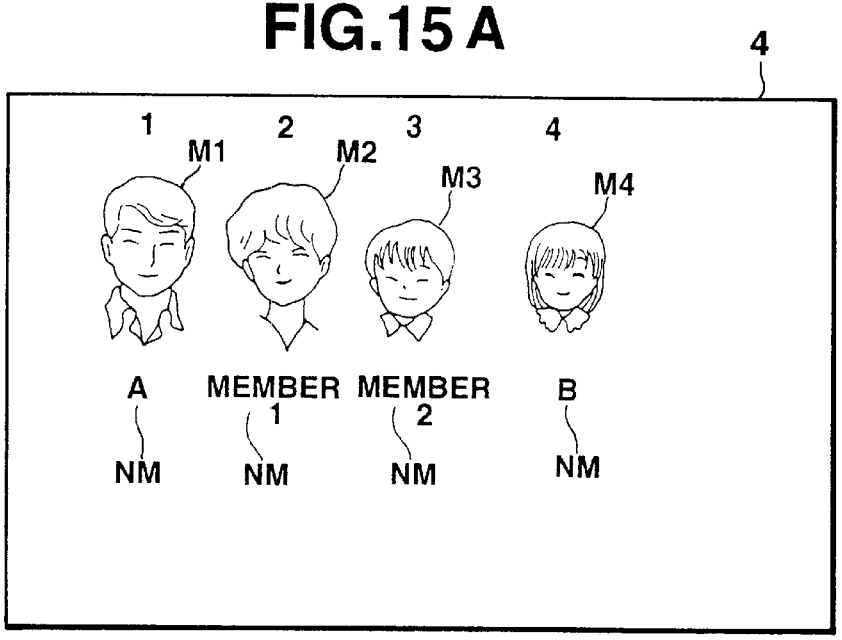
FIG. 15A is a view showing an example of indication of composed portraits.
FIG. 15B is a view showing an example of indication of a conclusion of palm reading.
Figure 15:
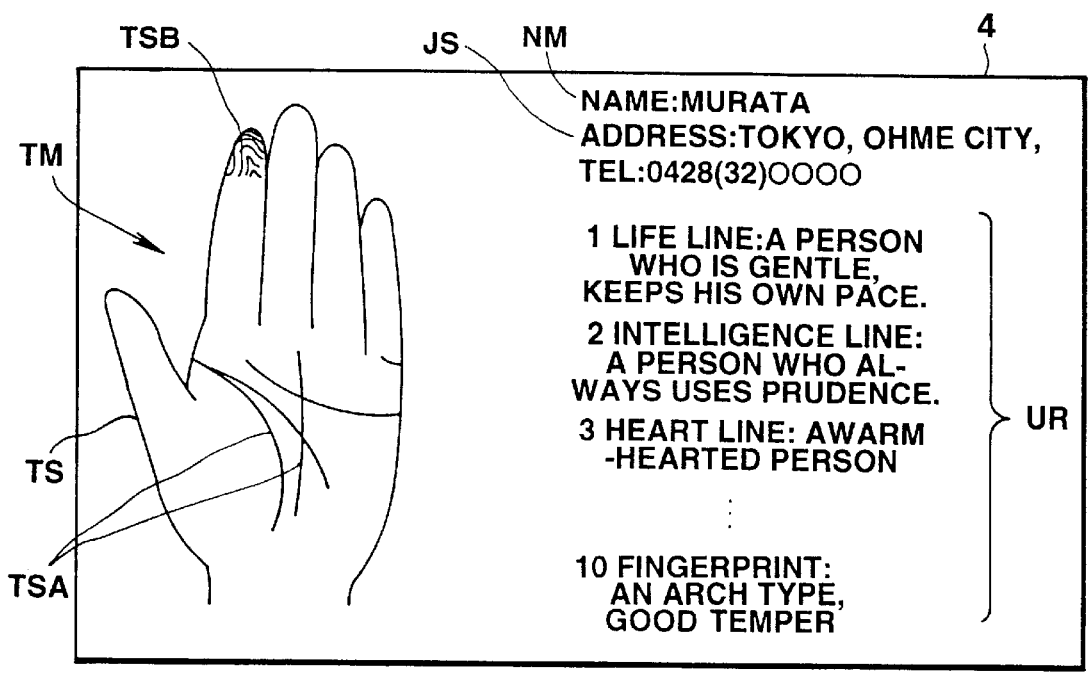
Figure 16A:
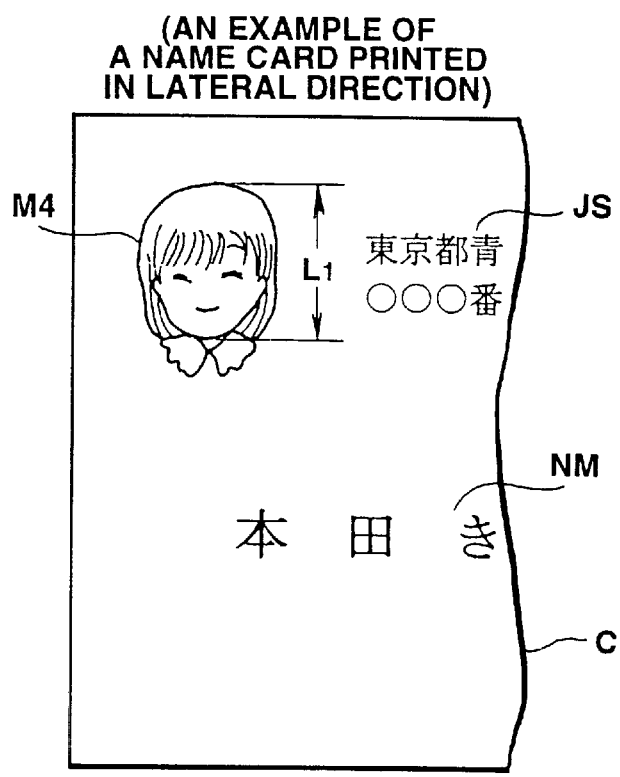
FIGS. 16A and 16B are views showing examples of printed name cards, respectively.
Figure 16B:
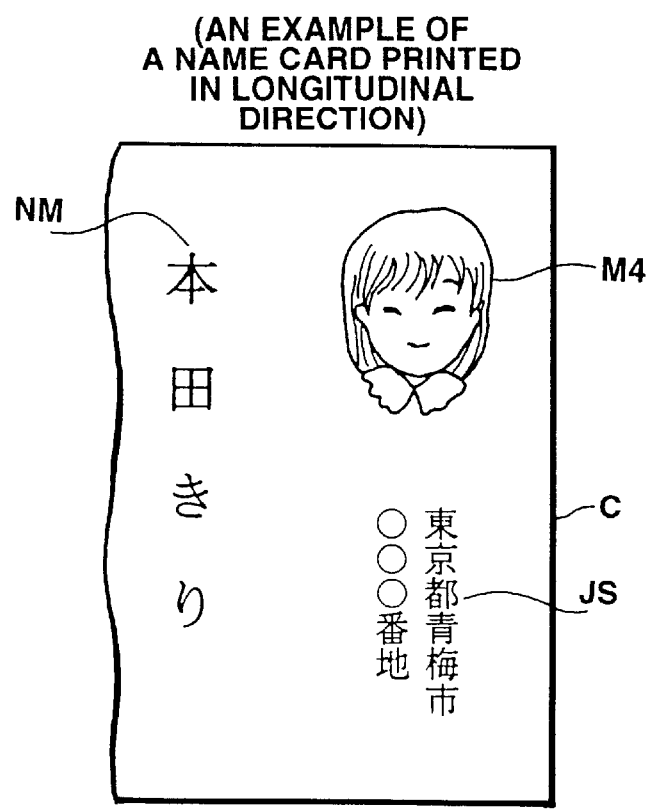

Similarly, it is judged respectively at steps SE8, SE10, SE12, SE14 and SE16 whether a fortune-line switch 67, an heart-line switch 65, a marriage-line switch 64, a heart-line switch 63 and the fingerprint switch 62 of FIG. 2 are operated. When it is determined that the fortune-line switch 67, the heart-line switch 65, the marriage-line switch 64, the health-line switch 63 and the fingerprint switch 62 are operated, part-pattern numbers are replaced with those designated by operations of the relevant switches, respectively, and the designated part-pattern numbers are registered. The part-pattern numbers included in the palm-montage of the fundamental type "01" are replaced with the part-pattern numbers, respectively, each of which corresponds to the part pattern that has the best resemblance to a relevant pattern on the palm of the person. Then, the palm montage TM of the person which has been modified by the user is displayed on the display unit 4 (refer to FIG. 15(B)).

When the desired palm montage TM is displayed on the display unit 4, the register switch 10 is operated or characters "O" and "K" are entered by character switches. Then, the operation goes from step SE18 to step SE19, where all the designated part-pattern numbers of the palm of the person are registered respectively in the relevant part areas of the palm data area 157, which corresponds to the area where the personal data of the person are previously registered in accordance with the flow chart of FIG. 9. When the process of registering/displaying the palm montage is finished, the operation returns to step SA3 of the general flow chart of FIG. 8.

Figure 13:
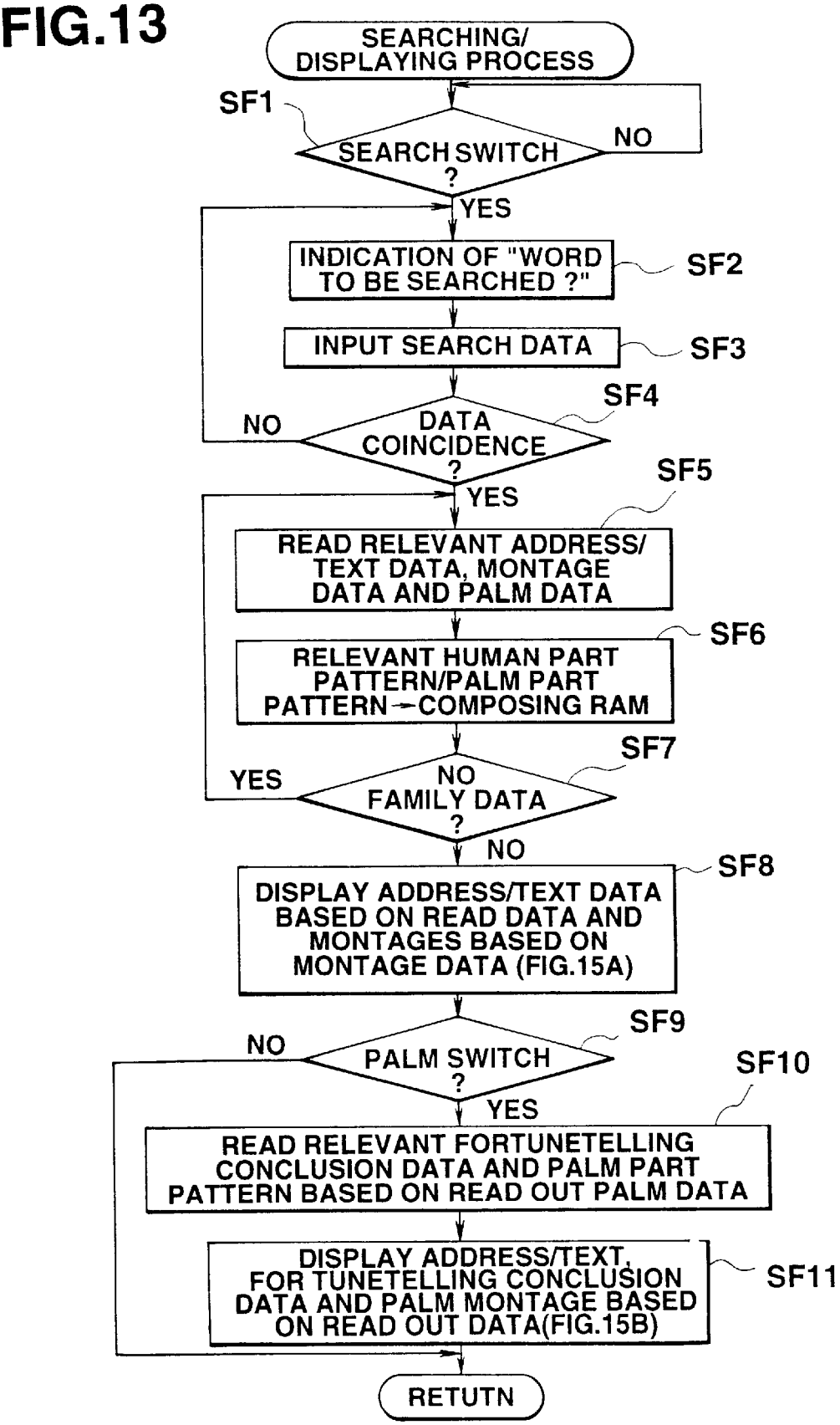
FIG. 13 is a flow chart of a searching/displaying process.

At step SA3, a searching/displaying process is performed in accordance with a flow chart of FIG. 13.

More specifically, it is judged at step SF1 whether a search switch 3A of the input unit 2 is operated. When it is determined that the search switch 3A has been operated, an indication of "word to be searched for?" is displayed on the liquid crystal display unit 4 at step SF2. Then, at step SF3, the user inputs, by operating the switch of the input unit 3, the same search data as anyone of names of persons (Mr. A, Mr. B and so on) among the personal data which are previously stored in the RAM 15. At step SF4, it is judged whether the input search data coincides with any of the names previously stored as personal data.

When the search data input by the switch operation coincides with one of names in the personal data stored in the RAM 15, the corresponding "address/text data", "montage data" (part-pattern numbers) and "palm data" (part-pattern numbers) are read out at step SF5. Part patterns of the person and part patterns of the palm, which correspond respectively to part-pattern numbers composing the montage data and the palm data, are read out from the data RAM 15 and are transferred to the montage-composing area 151 of the data RAM 15 at step SF6. At step SF7, it is judged whether family data of the person, whose name coincides with the input search data, have been previously stored. When "YES", processes in a loop (from step SF5 to step SF7) are repeatedly performed, wherein all the relevant family data: "address and text data", "montage data" and "palm data" are read out. As shown in FIG. 15A, together with the read out "address and text data", portraits or montages of full-length figure and palm montages of all members of the family bearing numbers "1", "2", "3" and so on are simultaneously displayed on the display unit 4 based on the montage data and the palm data at step SF8. In FIG. 15A, the portraits (face montages, in place of montages of the full-length figure) of all the members of the family are displayed bearing numbers presenting the order of registration, and names "NM" among the address and the text data are displayed together with the portraits on the display unit 4. The user can see on the display unit 4 the portraits or montages of the full-length figure of all the members in the family together with relevant address and text data.

Then, it is judged at step SF9 whether the palm switch 3B of the input unit 3 has been operated. When it is determined that the palm switch 3B has been operated, relevant palm part-patterns corresponding to the palm part-pattern numbers composing the palm data and fortunetelling data corresponding to the palm data are read out from the palm part-pattern area (A) and the conclusion-data area of the palm part-pattern/conclusion data ROM 14C, respectively, at step SF10. At the same time, the addresses and text corresponding to the palm data are read out from the address/text data area 155, and a palm montage TS composed of a combination of the read out palm part-patterns, the read out address and text data and the read out conclusion data of fortunetelling are simultaneously displayed on the display unit 4 at step SF11, as shown in FIG. 15B. As illustrated in FIGS. 15A and 15B, at step SF11, on the liquid crystal display unit 4 are displayed not only the palm montage TS of the relevant person but also the conclusion data of fortunetelling with respect to the palm lines TSA and the fingerprint TSB. Further, the name NM and the address JS are displayed on the display unit 4.

When the displaying process is finished, the operation returns to the process at step SA4 of the general flow of FIG. 8.

Figure 14:
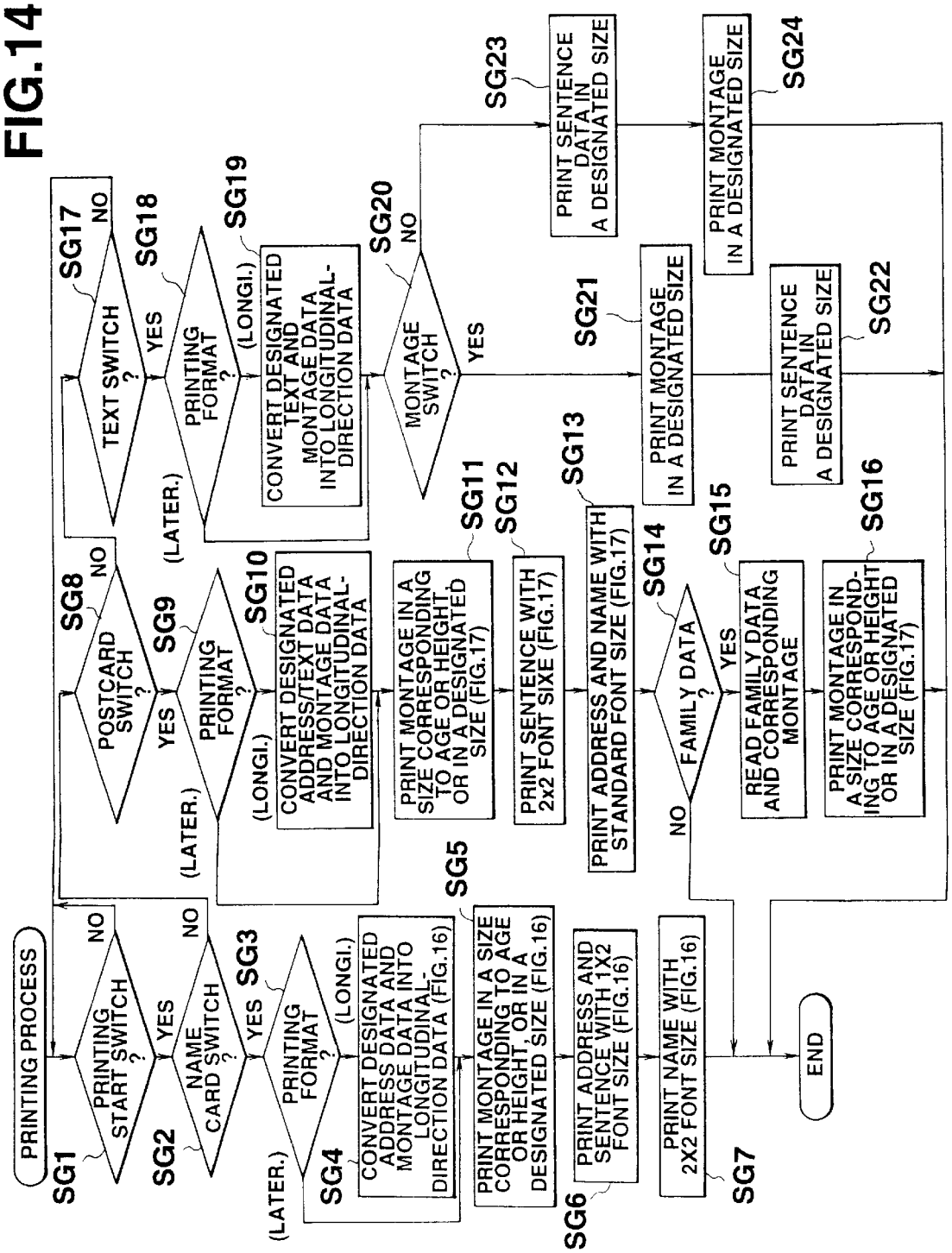
FIG. 14 is a flow chart of a printing process.

At step SA4, a printing process is performed in accordance with a flow chart of FIG. 14.

It is judged at step SG1 whether a printing-start switch 3C is operated. When it is determined that the printing-start switch 3C has been operated, it is judged at step SG2 whether a name-card switch 3D is operated. When it is determined that the name-card switch 3D has been operated, it is judged at step SG3 whether a printing format is set to a lateral-direction printing format or a longitudinal-direction printing format. When the lateral-direction printing format is set, since the address data and montage data have been designated as a result of the searching operation performed in the searching/displaying process, the designated address and montage data are converted into data in the lateral-direction printing format at step SG4. In the present embodiment, since all data are previously supposed to be printed in a lateral direction, data in the lateral-direction format are stored in the data RAM 15. Therefore, only when data are to be printed in a longitudinal direction, the above data-converting process of step SG4 is executed.

At step SG5, a montage is printed based on the designated montage data in a size defined by age data or height data among the designated address data. Therefore, a montage of an older person is printed in a larger size while a montage of a younger person is printed in a smaller size. The montage is printed in a similar manner with respect to the height of the person. The montage is also printed in a size previously determined by the user.

The address included in the designated address data is printed, for example, with a 1×2 font size or with a 2×1 font size at step SG6, and the name included in the designated address data is printed with a 2×2 font size at step SG7. During the processes at steps SG5 to SG7, a name card M printed in the lateral direction or in the longitudinal direction is produced. On the name card M, the name NM is printed with a 2×2 font size, the address JS with a 1×2 font size, and the montage TS is printed in a size L1 corresponding to the age of the person. As described above, only by searching for address and text data by inputting search data and operating the printing-start switch 3C, the address JS and the name NM are printed on the name card CM, and the montage TS of the object person is automatically printed on the name card CM. Further, since the montage TS is printed on the name card CM in the size L1 corresponding to the age or the height of the person, the montage can be represented in a size in proportion to the age and the height of the person.

Figure 17:
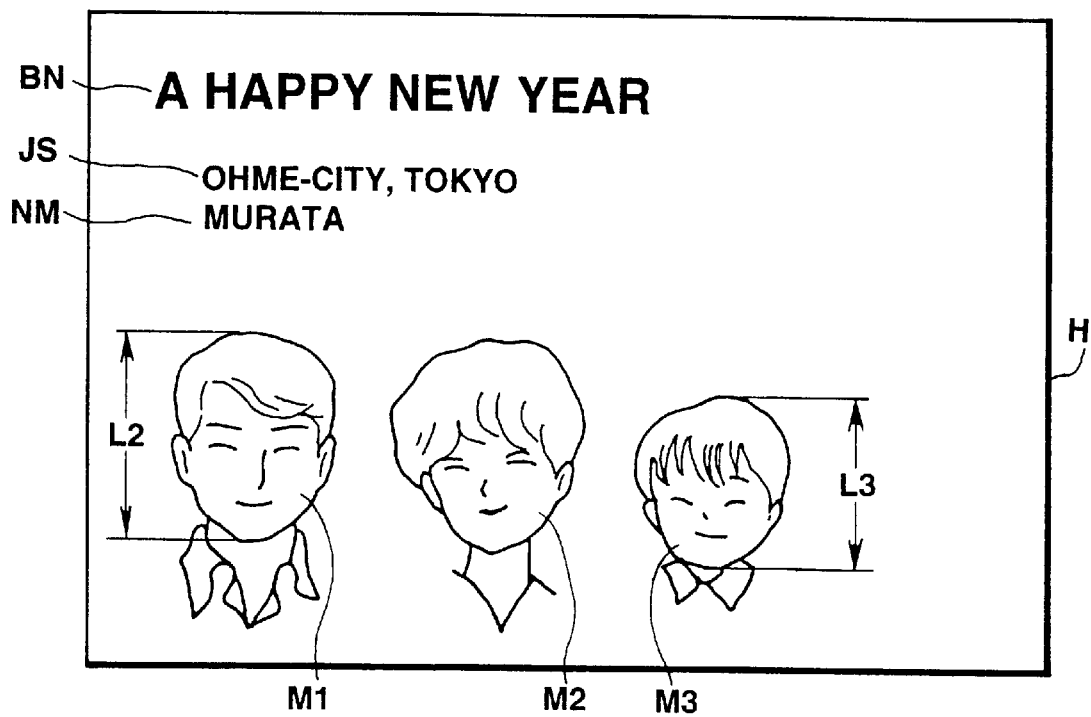
FIG. 17 is a view showing an example of a printed post card.

When the name-card switch 3D is not operated, it is judged at step SG8 whether a postcard switch 3E is operated. When the postcard switch 3E has been operated, it is judged at step SG9 whether the printing format is set to the lateral-direction printing format or the longitudinal-direction printing format. In case the printing format is set to the lateral-direction printing format, the designated address/text data and montage data are converted into data in the lateral-direction format at step SG10. A montage M1 is printed based on the montage data in a size determined based on the age and the height of the person. or in a designated size at step SG11 as illustrated in FIG. 17. The text is printed with a 4×4 font size at step SG12, and the address TS and the name NM are printed with a standard font size at step SG13. Further, it is judged at step SG14 whether any family data is stored in the RAM 15. When it is determined that the family data is stored in the RAM 15, the family data and the relevant montage data are read out from the address/text data area 155 and the montage-data area 156, respectively, at step SG15. Montages M3 and M4 corresponding to the read out montage data are printed in sizes determined based on the age or the height represented by the age data or the height data in the read out family data, or in previously designated sizes at step SG 16. In other words, if the object person is 100 years of age, the montage of the person will be printed in the largest size. On the contrary, if the object person is one year of age, the montage will be printed in the smallest size. Further, if, for example, the object person is 200 cm. tall, the montage will be printed in the largest size, and if the object person is 50 cm. tall, the montage will be printed in the smallest size. During the processes at steps SG11 to SG16, a post card H is produced, on which a text BN of "A Happy New Year" is printed with a 2×2 font size, an address JS and a name NM are printed with the standard font size, and further the montages of the family members are printed in sizes proportional to their ages, as shown in FIGS. 17. As described above, only by searching for the address/text data by inputting the search data, and operating the printing-start switch 3C and the switch 3E, the text BN of "A happy New Year", the address JS, the name NM and the montages M1–M3 of the person to be searched for are automatically printed on the postcard H. Since the montages M1–M3 are printed on the postcard H in the sizes L2, L3 in accordance with the ages and the heights of the persons, the portrait M1 of an adult or a tall person may be printed in the size of L2 and the portrait M3 of a child or a not tall person may be printed in the size L3. The montage of a person may be drawn in a size in proportion to the age or the height of the person.

When the printing-start switch 3C and the postcard switch 3E are not operated, it is judged at step SG17 whether a text switch 3F,is operated. When it is determined that the text switch 3F has been operated, it is judged at step SG18 whether the printing format is set to the lateral-direction printing format or the longitudinal-direction printing format. In the case that the lateral-direction printing format has been set, text data and montage data stored in the data RAM 15 are converted into data in the lateral-direction format at step SG19. Then, it is judged at step SG20 whether a montage switch 3G is operated. When it is determined that the montage switch 3G has been operated, the montage is printed at first in a size previously designated by the user at step SG21, and then the text data is printed in a size designated by the user at step SG22. Meanwhile, when the montage switch 3G has not been operated, the text data is printed at first in a size previously designated by the user at step SG23, and then the montage is printed in a size designated later. The operation of the montage witch 3G will determine whether the montage is printed before the text is printed or the text is printed before the montage is printed. Therefore, the user is allowed to determined positions where the montage and the text are printed by operation of the montage switch 3G.

Second Embodiment

Figure 18:
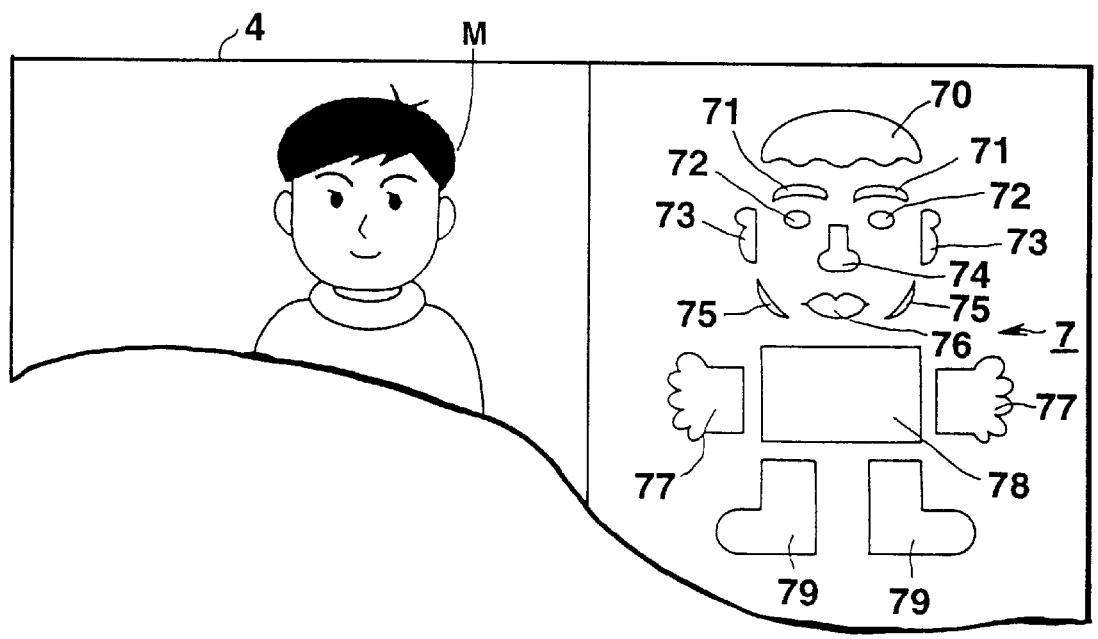
FIG. 18 is a view showing a second embodiment of the present invention.

FIG. 18 is a view showing a second embodiment of the present invention. In FIG. 18, like elements in the embodiment of FIGS. 1–17 are designated by like reference numerals, and their description will be omitted there.

In the second embodiment, there are provided a plurality of part-designating touch switches 70–79, which are disposed at locations corresponding respectively to positions of the parts in an object image to be composed. Further, next to the part-designating touch switches 70–79, there is a display unit 4 for displaying an object image M which is composed of a combination of part patterns of the respective parts designated by the part-designating touch switches 70–79. The part-designating touch switches 70–79 are made of touch sensors or touch type switches which are actuated with the finger tip of the user, a pen or a touch rod. When the user touches one of the touch switches 70–79 with his finger tip, the relevant part pattern is selected and read out from a plurality of part patterns stored in the part-pattern ROM 14B. The part patterns read out in this manner are combined into an object image M, and the combined object image M is displayed on the display unit 4. Further, the present embodiment is provided with the printer 18 which prints the object image M displayed on the display unit 4.

With the above described structure, when the touch switches 70–79 are operated, the relevant part patterns are read out from the part-pattern ROM 14B, the read out part patterns are combined into the object image M, and the combined object image M is displayed on the display unit 4 and simultaneously printed by the printer 18.

Since the display unit 4 and the plurality of touch switches 70–79 are provided in close proximity, the part pattern of the part designated by the touch switch is displayed on the adjacent display unit 4. Therefore, the user can compose his desired object image M viewing the respective part patterns on the display unit 4, thereby the user is allowed to compose a montage with ease in a short time.

In the above described embodiment, there are provided a plurality of part-designating touch switches 70–79, which are disposed at locations corresponding respectively to positions of the parts in the object image to be composed. However, it is not always necessary that the part-designating touch switches 70–79 be disposed at the locations corresponding respectively to the positions of the parts in the object image to be composed. For example, the part-designating touch switches 70–79 may be disposed in a matrix arrangement, respectively, in correspondence to the parts in an object image to be composed.

Third Embodiment

Figure 19A:
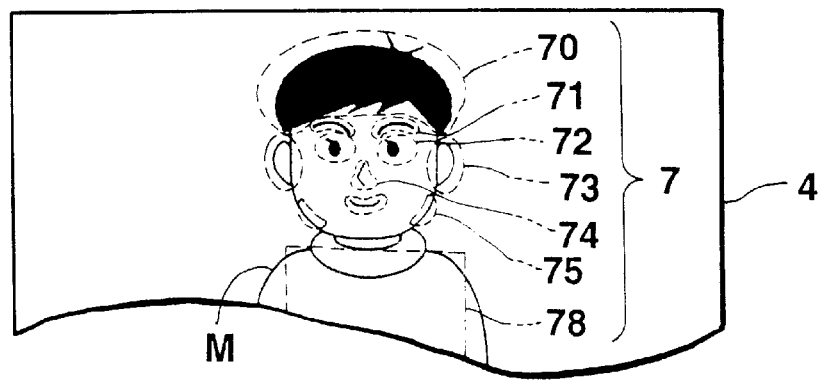
FIG. 19A is a view showing a third embodiment of the present invention.
Figure 19B:
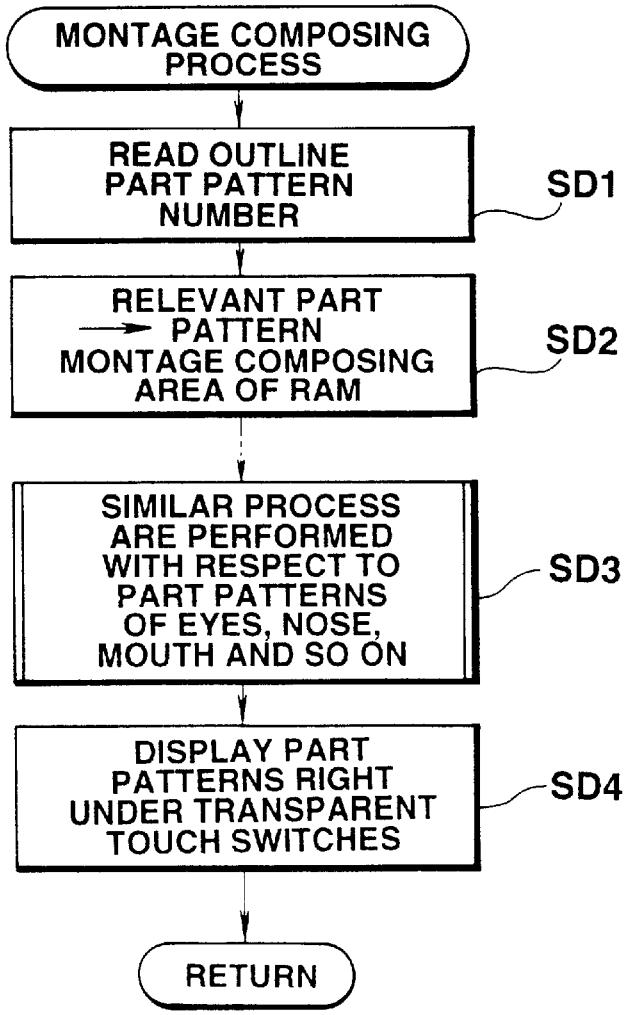
FIG. 19B is a flow chart of operation of the third embodiment of FIG. 19A.

FIGS. 19A and 19B are views illustrating a third embodiment of the invention. As shown in FIG. 19A, a plurality of transparent touch switches 70–79 are formed on the display unit 4, and part patterns corresponding to parts designated by operation of the transparent touch switches 70–79 are displayed as part marks at positions right under the relevant transparent touch switch 70–79. The part marks displayed on the display unit 4 may be marks corresponding respectively to the parts designated by the touch switches 70–79, but in the present embodiment, if the part of "hair style", for example, is designated by operation of the touch switch, a part pattern of the part of "hair style" is displayed at a position right under the operated touch switch.

When the user touches one of the touch switches 70–79 with his finger tip, a part pattern of the relevant part is selected and read out from among plural sorts of part patterns stored in the part pattern ROM 14B. An object image M composed of a combination of the part patterns read out in this manner is displayed at a position right under the transparent touch switches 70–79 on the display unit 4. The third embodiment is also equipped with the printer 18 of the same structure as the second embodiment. Other structure of the third embodiment is the same as the second embodiment.

With the above mentioned structure of the third embodiment, when one of the plurality of transparent touch switches 70–79 is operated, the relevant part-pattern number is substituted for the original part-pattern number in the processes of steps SC4–SC15 of FIG. 10, and the part pattern corresponding to the substituted part-pattern number is selected and read out from among the plural sorts of part patterns stored in the part-pattern ROM 14B in the processes at steps SD1–SD5 of FIG. 19B. The read out part pattern is substituted for the original part pattern, and the substituted part pattern and other original part patterns are combined in the montage composing area 151. Then, an object image M composed in this manner is displayed on the display unit 4. At the same time, the part pattern corresponding to the part designated by the part designating switch is displayed at the position right under the operated transparent touch switch 70–79 on the display unit 4 (see step SD6A of FIG. 19B). The object image M displayed on the display unit 4 is printed by the printer 18 in a similar manner as described with reference to FIG. 14.

Further, with the above structure of the embodiment, since part patterns having corresponding shapes are displayed respectively at relevant positions on the display unit 4 right under the transparent touch switches 70–79, the user can operate the touch switches viewing the part patterns on the display unit 4. In this way, the user can compose his desired object image M with ease in a shorter time.

Fourth Embodiment

In the above embodiments of the invention, the objects whose images are to be composed are humans, and their portraits and montages of a full-length figure are composed and printed. But other animals, plants or buildings may be objects, and their montages are composed with the present displaying/printing apparatus. In this case, if an image of a building is composed, it is preferable that the part-designating switches (7: 70–79) for designating the parts of the building such as a roof, a chimney, poles and a floor are disposed at positions corresponding respectively to the positions of these parts in an image of the building to be composed.

Advantages of Embodiments

With the above mentioned structures of the invention, only by operation of the part-designating switches 62–68, 70–79 prepared respectively for parts composing an object (a whole object or a portion of the object) whose image is to be composed, the part itself and the corresponding part pattern can be designated simultaneously and directly without making a mistake. Accordingly, using the part patterns thus designated, the montage of the object can be composed and displayed with ease in a short time.

Meanwhile, in conventional montage-composing apparatus, part-designating switches are not disposed at positions corresponding to positions of parts in a montage to be composed, but are disposed independently of positions of the parts in the montage of the object. Further, part-pattern designating switches are disposed independently of the positions where the part-designating switches are disposed. Therefore, when the user wants to operate the part-designating switch, he often operates the part-pattern designating switch instead of the part-designating switch in error, and vice versa. It is hard to compose the montage with the conventional montage-composing apparatus in a short time. However, the object-image displaying apparatus according to the present invention is provided with the part-designating switches 62–68, 70–79, which are disposed at the positions corresponding respectively to the positions of the parts in the montage to be composed. The part-designating switches 62–68, 70–79 can be used as the part-pattern selecting switches to select part patterns. Therefore, the user can operate the correct part-designating switch which corresponds directly to the part to be designated, without operating other part-designating switch in error.

Further, the part-designating switches 62–68, 70–79 have external shapes corresponding respectively to shapes of the parts composing the object whose montage is to be composed. Therefore, the user can directly designate his desired part by operating a correct part-designating switch without making a mistake.

Furthermore, by operation of the part-designating switches 62–68, which are prepared respectively for the parts composing the palm montage to be composed, a desired part is designated, and a part pattern of the designated part is displayed and a relevant conclusion of the palm-fortunetelling (palm-reading) with respect to the displayed part pattern is displayed. Therefore, palm data (conclusion of palm-fortunetelling) corresponding to his own palm of the user or the palm of other can be displayed together with the corresponding palm pattern with ease.

Several embodiments of the present invention have been described in detail but these embodiments are simply illustrative and not restrictive. The present invention may be modified in various manners. All the modifications and applications of the present invention will be within the scope and spirit of the invention, so that the scope of the present invention should be determined only by what is recited in the present appended claims and their equivalents.

What is claimed is:

1. An image display control apparatus for selecting a desired plurality of part images from among a plurality of sorts of similar part images, each of the plurality of sorts of similar part images representing a respective one of the parts which compose a person, and being stored in a part image storage device, the image display control apparatus controlling a display device to display the person's image which is composed of combined selected part images, the apparatus comprising:

personal data input means for inputting personal data corresponding to a person's image to be formed;

storage means for storing a personal data input by said personal data input means and a plurality of specifying data in corresponding relationship, the plurality of specifying data specifying the respective part images which compose the person's image, without storing the respective part images themselves;

first reading means for reading from said storage means the personal data and corresponding to the plurality of specifying data;

second reading means for reading from said part image storage device a plurality of part images corresponding to the plurality of specifying data read by said first reading means; and display control means for combining the plurality of part images read by said second reading means into a person's image and for causing the display device to display together the person's image and the corresponding personal data read by said first reading means.

2. An image display control method for selecting a desired plurality of part images from among a plurality of sorts of similar part images, each of the plurality of sorts of similar part images representing a respective one of the parts which compose a person, and being stored in a part image storage device, the image display control method controlling a display device to display the person's image which is composed of combined selected part images, the method comprising the steps of:

a) inputting personal data corresponding to the person's image to be formed;

b) storing in a data storage device a personal data input to said personal data inputting step and a plurality of specifying data in corresponding relationship, the plurality of specifying data specifying the respective part images which compose the person's image without storing the respective part images themselves;

c) a first reading step for reading from said data storage means the personal data and corresponding plurality of specifying data;

d) a second reading step for reading from the part image storage device the plurality of part images corresponding to the group of specifying data read in said first reading step; and e) combining the plurality of part images read in said second reading step into a person's image and causing the display device to display together the person's image and the corresponding personal data read in said first reading step.

3. A recording medium which prestores a computer readable image display control program for causing a computer to select a desired plurality of part images from among a plurality of sorts of similar part images, each of the plurality of sorts of similar part images representing a respective one of the parts which compose a person, and being stored in a part image storage device, and to control a display device to display the person's image which is composed of combined selected part images, the program causing the computer to perform the steps of:

storing respectively in a data storage device a personal data, corresponding to person images, and a plurality of specifying data in corresponding relationship, the plurality of specifying data specifying the respective part images which compose the person's image, without storing the respective part images themselves;

reading from said storage means the coinciding personal data and corresponding plurality of specifying data;

reading from the part image storage device a plurality of part images corresponding to the read plurality specifying data; and combining the read plurality of part images into a person's image and causing the display device to display together the person's image and the corresponding read personal data.

4. A montage face image display control apparatus for causing a display device to display a montage face image of combined part images, the apparatus comprising:

creating means for combining a plurality of part images each representing a respective one of parts of a face into a montage face image;

recording means for recording in a storage means in corresponding relationship a personal data and a plurality of specifying data, the plurality of groups of specifying data specifying the respective part images which compose a montage face images created by said creating means without recording the respective part images themselves; and display control means for reading from said recording means the personal data and corresponding plurality of specifying data, for combining the plurality of part images read into a person's image and for causing the display device to display both the coinciding personal data and the corresponding montage face image.

5. A montage face image display control method for causing a display device to display a montage face image of combined part images, the method comprising the steps of:

combining part images each representing a respective one of parts of a face into a montage face image;

recording in a storage means in corresponding relationship a personal data and a plurality of specifying data, the plurality of specifying data specifying the respective part images which compose a montage face images without recording the respective part images themselves;

reading from said storage means the personal data and corresponding plurality of specifying data;

combining the plurality of part images into a montage face image; and causing the display device to display together the personal data and the corresponding montage face image.

6. A recording medium which prestores a computer readable montage face image display control program for causing a computer to display a montage face image of combined part images on a display device, the program causing the computer to perform the steps of:

combining part images each representing a respective one of parts of a face into a montage face image;

recording in a storage means in corresponding relationship a personal data and a plurality of specifying data, the plurality of specifying data specifying the respective part images which compose montage face images obtained in said combining step without recording the respective part images themselves;

reading from said storage means the personal data and corresponding plurality of specifying data;

combining the plurality of part images into a montage face image; and causing the display device to display together the personal data and the corresponding montage face image.

\* \* \* \* \*